United States Patent [19]

Maroney et al.

[11] Patent Number: 4,638,399
[45] Date of Patent: Jan. 20, 1987

[54] WRIST STRAP GROUND MONITOR

[75] Inventors: Ralf P. Maroney, Orange; Gregory A. Fishkind, Milford; Frederick Schneider, Stratford, all of Conn.

[73] Assignee: Plug-In Storage Systems, Inc., Milford, Conn.

[21] Appl. No.: 784,053

[22] Filed: Oct. 4, 1985

[51] Int. Cl.[4] .......................... H05F 3/02; A61N 1/14; G01R 31/02
[52] U.S. Cl. .................... 361/220; 340/649; 340/652; 340/658; 324/51
[58] Field of Search ............... 361/220, 222, 223, 215, 361/48–50; 307/117, 326; 128/381, 384, 908; 340/649, 652, 568, 658; 324/51 (U.S. only); 174/55 B, 55 G, 5 R

[56] References Cited

U.S. PATENT DOCUMENTS

| 3,706,008 | 12/1972 | Kremer | 361/49 |
| 3,755,688 | 8/1973 | Hohler | 307/117 |
| 3,774,106 | 11/1973 | MacPhee | 324/51 |
| 3,783,340 | 1/1974 | Becker | 361/50 |
| 3,784,842 | 1/1974 | Kremer | 307/326 |
| 4,475,141 | 10/1984 | Antonevich | 361/220 |
| 4,558,309 | 12/1985 | Antonevich | 340/659 X |

Primary Examiner—L. T. Hix
Assistant Examiner—Della Rutledge
Attorney, Agent, or Firm—Kramer and Brufsky

[57] ABSTRACT

Apparatus which can be embodied in an electronic wristwatch monitors the integrity of a wrist strap ground. An input terminal to which a known ground is coupled is provided. An oscillator produces a fixed frequency which is mixed with a signal from the input terminal to provide a composite signal. The composite signal is coupled to one input of an exclusive OR-gate. The other input of the exclusive OR-gate is coupled directly to the output of the oscillator. The output of the OR-gate is processed to produce an output signal indicative of the phase relationship between the oscillator output and the composite signal. When the input terminal is grounded, the phase relationship between the oscillator output and the composite signal changes, resulting in a change in the output signal which can be used to trigger an indicator (e.g., visual display and/or aural alarm) to indicate to a user whether he or she is properly grounded.

22 Claims, 6 Drawing Figures

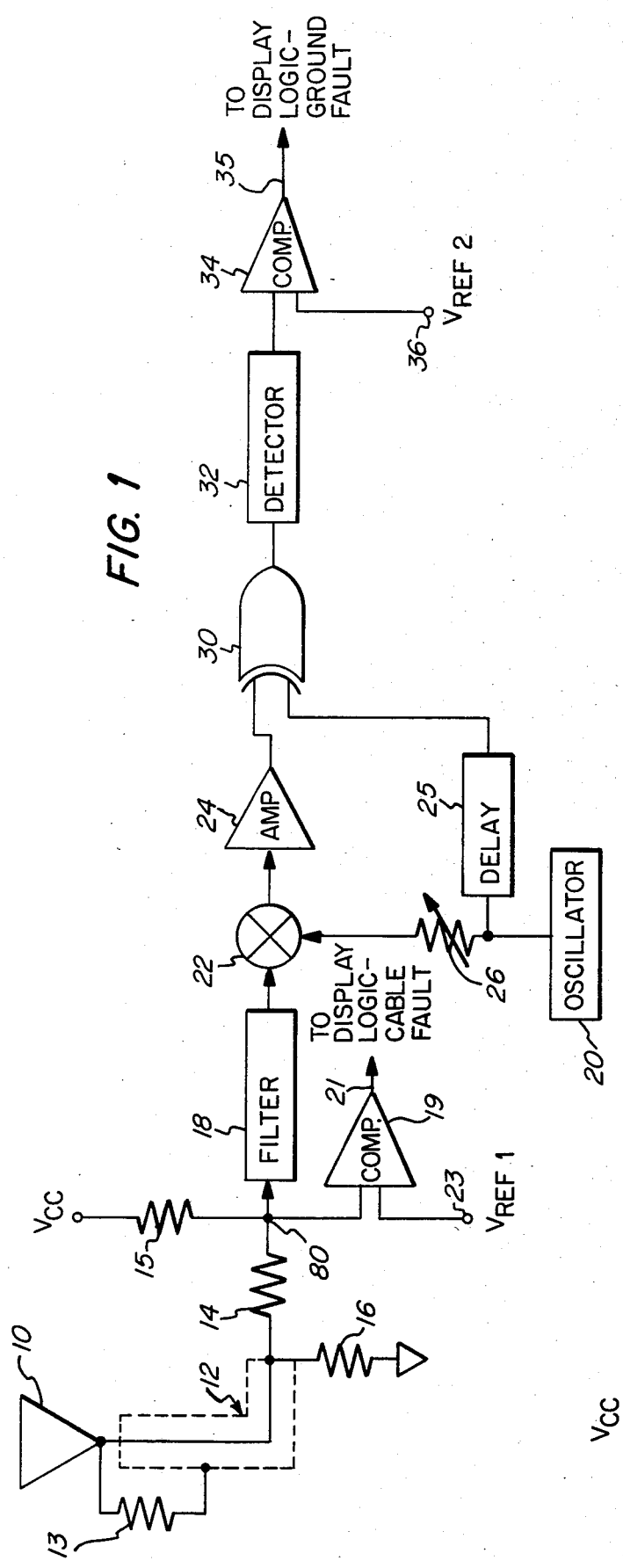

WRIST STRAP GROUND MONITOR

BACKGROUND OF THE INVENTION

This invention relates to electrically conductive grounding straps that are used to discharge static electricity from personnel handling sensitive electronic components, and more particularly to apparatus for monitoring the integrity of the connection between the grounding strap and a known electrical ground.

Electrically conductive grounding straps are used to provide a path to ground for dissipating static charges on personnel. Such devices are integral elements of electronic workstations, protecting sensitive electronic components from degradation or destruction caused by electrostatic discharge. An example of such a grounding strap (often referred to as "wrist straps" since they are generally worn around a person's wrist) is disclosed in U.S. Pat. No. 4,475,141 entitled "Body Electrical Grounding Tether" and issued on Oct. 2, 1984. Such wrist straps consist of a lightweight elastic band and a ground lead with a plug or clip for connecting the lead to a known electrical ground.

The electrostatic discharge which such wrist straps are intended to dissipate can be on the order of several thousand volts of electrostatic build-up. Such charge is generated through normal movements of personnel. For example, static charge can be built up by walking across a carpet in a low-humidity environment. The use of wrist straps to drain potentially harmful charges away is a good approach, but standing alone has a major flaw; namely, there is no way to know if the wrist strap is functioning properly. Thus, if the wrist strap is improperly worn by personnel, or if there is cord breakage, any bad connection, or loss of continuity, failure of the charge dissipation would occur and might not be discovered until costly damage to delicate electronic circuitry has already occurred.

It would be advantageous to provide apparatus for detecting any open circuit between the user of a wrist strap and ground. Should such a situation develop, an audio and/or video indicator would be useful for informing the user that a problem exists which must immediately be remedied.

It would be further advantageous if such a wrist strap monitoring apparatus were built into the wrist strap itself, and also monitored the condition of the grounding cable for any fault. Such design would be convenient and ensure that the monitor is always in use and working while the wrist strap is being worn. It would be further advantageous if such monitoring apparatus and wrist strap were packaged together with a wristwatch for convenience in use by applicable personnel.

The present invention relates to such a wrist strap and integral ground monitor.

SUMMARY OF THE INVENTION

In accordance with the present invention, apparatus for monitoring the integrity of a wrist strap ground is provided. The apparatus includes an input terminal, an oscillator, and means for mixing the output of the oscillator with a signal from the input terminal to provide a composite signal. An exclusive OR-gate has the composite signal coupled to a first input thereof and the output of the oscillator coupled to a second input thereof. Means are provided for processing the output of the OR-gate to produce an output signal indicative of the phase relationship between the oscillator output and the composite signal. Grounding of the input terminal varies the phase relationship between the oscillator output and the composite signal, resulting in a change in the output signal that is used to provide an indication that a proper electrical ground has been achieved.

Means can be provided which are responsive to the output signal for providing a visual indication as to whether the input terminal is grounded. Similarly, an aural indication can be provided as to whether the input terminal is grounded.

The apparatus can further comprise a high-pass filter coupled between the input terminal and the mixer means for suppressing any A.C. hum (e.g., 60 Hz) that is present at the input terminal. An amplifier can be coupled between the mixer means and the exclusive OR-gate. Delay circuit means can be coupled between the oscillator output and the second input of the OR-gate for delaying the oscillator output signal by a predetermined time period before it reaches the OR-gate. Such means would match the delay inherent in the circuitry through which the components of the composite signal travel on their way to the OR-gate.

The processing means can comprise detector means coupled to the output of the exclusive OR-gate for integrating the OR-gate output to produce a corresponding D.C. logic level, together with comparator means coupled to the output of the detector and to a reference voltage for determining whether the D.C. logic level is above or below a predetermined threshold value. When the input terminal is connected to a proper electrical ground, the D.C. logic level will be above the predetermined threshold value and an indication that a proper ground is present will be provided to the user of the apparatus. A high impedance in series with the input terminal can be provided to protect the user from electric shock.

The apparatus of the present invention can be packaged in a case together with an electronic wristwatch. A digital display used for the wristwatch can be shared by the apparatus for indicating to a user thereof that a proper electrical ground has been achieved. The wristwatch case would include an input terminal which can be removably coupled to a ground cable. Means can be provided for indicating to a user whether the ground cable is intact. Further, means can be provided for indicating to a user whether the grounding apparatus is in proper contact with his or her body (e.g., at the wrist).

BRIEF DESCRIPTION OF THE DRAWINGS

FIG. 1 is a block diagram illustrating the ground monitoring circuitry in accordance with the present invention;

FIG. 2 is a block diagram showing how the circuitry of FIGS. 1 and 3 can be interfaced with a display and/or alarm;

FIG. 3 is a schematic diagram of a circuit for providing an indication as to whether the wrist strap ground monitor is in proper contact with a user's body member;

DETAILED DESCRIPTION OF THE INVENTION

Figure 4:
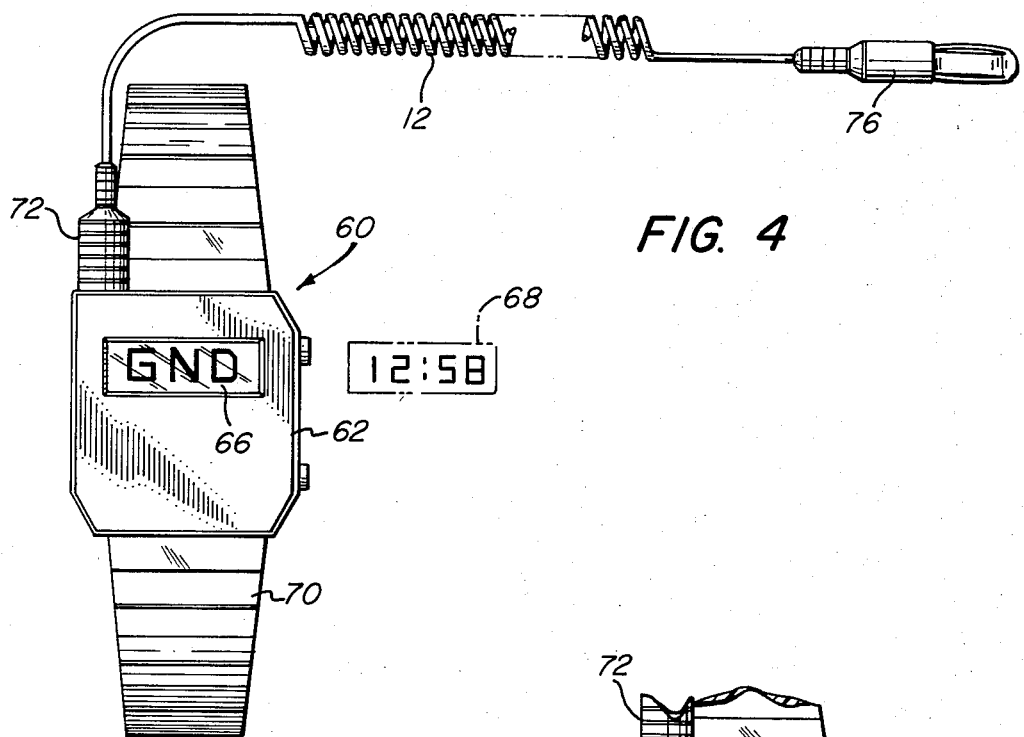
FIG. 4 is an illustration of a wrist strap ground monitor in accordance with the present invention incorporated into an electronic wristwatch package.

FIG. 1 illustrates in block diagram form a ground monitoring circuit in accordance with the present invention. A shielded ground cable 12 is coupled at a first end thereof to a source of electrical ground when in use, which ground is illustrated in FIG. 1 as a conductive mass 10. The other end of ground cable 12 is coupled to an input terminal 80 of the circuitry.

Input terminal 80 is connected to the center or "main" conductor of shielded cable 12 through a current limiting resistor 14 on the order of 1 megohm. Resistor 14 protects the user of the device against electric shock should there be an internal short in the detector circuitry. Resistor 14 is also used as part of a ground cable fault detection circuit described below. An additional current limiting resistor 16 on the order of 100 K-ohms is coupled between the conductive shield of ground cable 12 and the monitor circuit ground (which is isolated from the earth ground represented by conductive mass 10). Resistor 16 will protect a user from shock should the shield of ground cable 12 become exposed and connected to a hazardous voltage source. An additional cable fault test resistor 13 (on the order of megohm) is coupled between the main conductor and shield of cable 12 at the first end thereof. Resistor 13 serves as the predominant input impedance path to the ground monitoring circuit.

The combination of resistors 13, 14 and 16 form a ground cable impedance that can be monitored to determine whether the ground cable is in proper working order or is open or shorted. The cable impedance forms part of a voltage divider with resistor 15 that is connected to voltage source Vcc. The voltage divided between resistor 15 and the cable impedance is monitored at input terminal 80 by a comparator 19 which compares the voltage at input terminal 80 with a reference voltage $V_{ref1}$ input to the comparator at terminal 23. If the cable impedance is proper, the voltage at input terminal 80 will be within a predetermined range and the output of comparator 19 on line 21 will indicate that the cable is in good working order. On the other hand, for example, if cable 12 is shorted internally, resistor 13 will also be shorted and the cable impedance will consequently drop. This will cause the voltage at input terminal 80 to drop and comparator 19 will output a signal on line 21 to indicate a cable fault condition. A cable fault condition will also be output should the cable 12 become open or disconnected from input terminal 80.

Input terminal 80 and hence, the electrical ground source 10 is coupled to a body portion (e.g., wrist) of a user through a conductive metal electrode 50 (FIG. 5) which is placed into skin contact with the user's body. Thus, a user of the present apparatus will be grounded when ground cable 12 is coupled to a proper electrical ground.

A signal applied to input terminal 80 will pass to a filter 18 which may be a high-pass filter or a band-pass filter. The purpose of filter 18 is to suppress any A.C. hum (e.g., 60 Hz) which may be present at input terminal 80. In normal operation, input terminal 80 would be connected to ground via ground cable 12. However, if a proper ground connection is not made, some other signal will be present at input terminal 80 and detected by the remainder of the circuitry of FIG. 1.

The signal from input terminal 80 passes through filter 18 and is mixed at mixer 22 with a stable oscillator signal from oscillator 20. Variable resistance 26 is provided to adjust the sensitivity of the ground monitoring circuit. Resistor 26 will also introduce a delay into the oscillator signal as it travels to mixer 22. Mixer 22 in effect beats the filtered signal from input terminal 80 with the stable periodic signal from oscillator 20. The resultant "composite signal" is amplified by amplifier 24 and input to one input of an exclusive OR-gate 30. In balanced condition, amplifier 24 has enough gain to square up the signal and guarantee digital signal levels to drive exclusive OR-gate 30.

The other input of exclusive OR-gate 30 is coupled to the output of oscillator 20 via a delay circuit 25. The function of the delay circuit 25 is to match the delay inherent in mixer 22, resistor 26, and amplifier 24 so that absent any other influences (e.g., ground at input terminal 80), the two signals input to exclusive OR-gate 30 will be in phase and balancing will have been achieved.

In operation, if input terminal 80 is properly grounded, then the condition of the balanced circuit comprising mixer 22, amplifier 24, delay 25, and resistor 26 will be disrupted. The resultant imbalance will cause the digital waveform from amplifier 24 to no longer match the stable waveform output from delay circuit 25. The failure of the two signals input to exclusive OR-gate 30 to match (i.e., remain in phase) will cause the OR-gate output to go high in proportion to the imbalance.

A detector 32 is coupled to receive the output of exclusive OR-gate 30 and integrates the OR-gate output to produce a corresponding D.C. logic level. Comparator means 34 coupled to the output of detector 32 and to a reference voltage $V_{ref2}$ at terminal 36 determines whether the D.C. logic level is above or below a predetermined threshold value. The threshold value (established by $V_{ref2}$) is set so that a D.C. logic level above the threshold is indicative of a proper ground condition at terminal 80. Likewise, a D.C. level below the threshold value indicates that input terminal 80 is not properly grounded. Thus, the output of comparator 34 on line 35 can be used to drive a visual display (e.g., light emitting diode or liquid crystal display) and/or an aural alarm to indicate to a user whether a proper ground is present at input terminal 80.

Those skilled in the art will appreciate that the combination of oscillator 20, exclusive OR-gate 30, and detector 32 form a frequency discrimination phase-lock-loop known in the art for other purposes such as radio frequency signal tuning. It will also be appreciated that the circuitry of the ground monitor will require a stable voltage supply (e.g., using conventional regulators) in order to assure balanced operation. This is particularly important when the circuit is battery powered, to maintain proper operation as the battery wears down.

The output of comparator 34 on line 35 can be used to drive a display 42 and/or optionally an alarm 43 as shown in FIG. 2. In such instance, display interface and decoder circuitry 40 will decode a signal from comparator 34 to display an appropriate signal (e.g., "GND" as shown at 66 in FIG. 4) or inhibit an audible alarm when a proper ground is present at input terminal 80. Integrated circuits which include decoder 40 and appropriate drivers for display 42 and/or alarm 43 are well known in the art. The display interface circuitry and decoder 40 can be incorporated in an integrated circuit that also includes the electronics for a wristwatch, and the ground monitor can share the display used to display the time.

Figure 5:
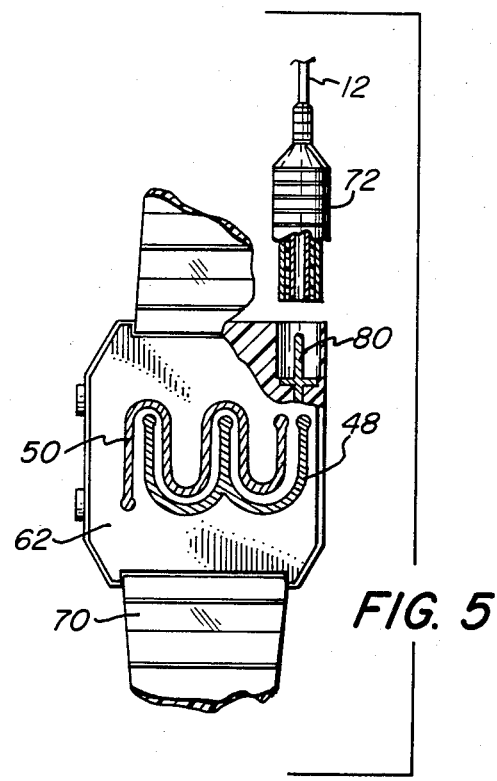
FIG. 5 is a rear view of the wristwatch package of FIG. 4 illustrating the ground electrode, test electrode, and input terminal used in connection with the ground monitoring circuitry.

The ground monitoring circuitry of FIG. 1 is intended to be incorporated in integrated circuit form in combination with a wrist strap. In a preferred embodiment, the wrist strap is packaged together with an electronic watch as best illustrated in FIG. 4. In such an embodiment, it is desirable to ensure that the wristwatch/wrist strap/ground monitor 60 is properly worn on the wrist of a user. In order to achieve such assurance, an additional terminal or contact 48 can be provided on the back of the wristwatch/wrist strap/ground monitor 60 as shown in FIG. 5. In use, the case 62 of the apparatus is secured against the wrist of a user by a strap 70 in a conventional manner. Contacts 48 and 50 (which are interleaved for reliable skin contact over a large surface area) will be in intimate contact with the user's wrist. Contact 50 is connected to input terminal 80 of the circuitry shown in FIG. 1 so that when ground cable 12 is properly grounded, the user will also be properly grounded through his or her wrist.

The circuit of FIG. 3 will ensure that the wristwatch/wrist strap/ground monitor 60 is properly worn by the user by inhibiting a body contact signal on output line 49 of gate 44, which is normally used to drive a display or inhibit an alarm signal to the user, unless both contacts 48 and 50 are in intimate contact with the user's skin. As already stated, contact 50 is normally connected to ground. Contact 48 is coupled to the input of a gate and to a power source Vcc through voltage divider resistor 46. If proper skin conductivity is present across contacts 48 and 50, gate 44 will turn on and provide a body contact signal on output line 49. This signal is input to the display logic via decoder 40 to provide a display to the user that proper body contact has been achieved.

Figure 6:
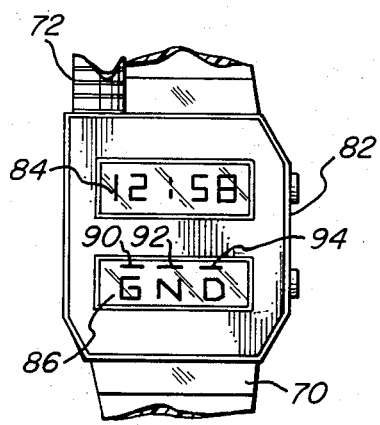
FIG. 6 is an illustration of an alternate embodiment of a wrist strap ground monitor incorporated into an electronic wristwatch package.

Two embodiments of a combination wristwatch/wrist strap/ground monitor are illustrated in the drawings. In FIG. 4, the ground monitor shares the display used by the wristwatch, so that when the ground monitoring circuit is not in operation, the wristwatch will display the current time, as indicated in phantom at 68. Alternatively, as shown in FIG. 6, a unitary case 82 can hold a wristwatch display 84 together with a separate ground monitor display 86. Display 84 will always show the current time.

Display 86 can be, for example, a liquid crystal display that has minimum power requirements and includes three bars 90, 92 and 94 together with the legend "GND". Bar 90 is displayed to indicate that the ground cable 12 is in proper working order and is triggered by the output signal from comparator 19 on line 21. Bar 92 is displayed to indicate that the wristwatch/wrist strap/ground monitor 60 is properly worn by the user and is triggered by the output signal from gate 44 on line 49. Bar 94 is displayed to indicate that input terminal 80 is connected to a proper electrical ground and is triggered by the output signal from comparator 34 on line 35. When all three conditions are met and each of bars 90, 92 and 94 is displayed, the legend "GND" will also be shown in display 86 to inform a user that the ground monitor is operating properly and a proper ground has been effected. If the "GND" legend is not displayed, at least one of bars 90, 92, or 94 will also be off, thereby signalling to the user which of the three conditions has not been met. The ground monitor display is driven by decoder logic 40 which receives signals designating the state of each of the three conditions on lines 21, 35, and 49. Alarm 43 can optionally be provided to give an audible signal when all three conditions are not met. Miniature piezoelectric alarms for wristwatches are well known in the art, and a similar device can be used for alarm 43.

The wristwatch/wrist strap/ground monitor 60 shown in FIGS. 4, 5 and 6 can be removably coupled to a proper ground source via ground cable 12 which is terminated at one end thereof with a jack 72 that plugs into terminal 80, and at the other end thereof with a banana plug 76 which plugs into a known ground source. Banana plug 76 can include a built-in resistor (resistor 13 shown in FIG. 1) to provide shock protection to a user. Similarly, jack 72 can incorporate a protective resistor (resistor 14 shown in FIG. 1). In such case, banana plug 76 and jack 72 are preferably molded in one piece together with their respective protective resistors to prevent tampering with the protective feature of the assembly.

It will now be appreciated that the present invention provides apparatus for tethering personnel to an electrical ground and monitoring the integrity of the ground. The apparatus can be combined with a conventional electronic wristwatch for the convenience of a user thereof.

Although this invention has been described in considerable detail, such description is intended as being illustrative rather than limiting, since the invention may be variously embodied without departing from the spirit thereof as set forth in the following claims.

What is claimed is:

1. Apparatus for monitoring the integrity of a wrist strap ground comprising:
 an input terminal;
 an oscillator;
 means for mixing the output of said oscillator with a signal from said input terminal to provide a composite signal;
 an exclusive OR-gate;
 means for coupling the composite signal to a first input of said OR-gate;
 means for coupling the output of said oscillator to a second input of said OR-gate; and
 means for processing the output of said OR-gate to produce an output signal indicative of the phase relationship between said oscillator output and said composite signal;
 whereby grounding said input terminal varies the phase relationship between said oscillator output and said composite signal resulting in a change in said output signal.

2. The apparatus of claim 1 further comprising:
 means responsive to said output signal for providing a visual indication as to whether said input terminal is grounded.

3. The apparatus of claim 1 further comprising:
 means responsive to said output signal for providing an aural indication as to whether said input terminal is grounded.

4. The apparatus of claim 1 further comprising:
 a high-pass filter coupled between said input terminal and said mixer means.

5. The apparatus of claim 1 further comprising:
 delay circuit means coupled between said oscillator output and said exclusive OR-gate for delaying the oscillator output signal by a predetermined time period before it reaches the second input of said OR-gate.

6. The apparatus of claim 1 further comprising:
an amplifier coupled between said mixer means and said exclusive OR-gate.

7. The apparatus of claim 1 wherein said processing means comprises:
detector means coupled to the output of said exclusive OR-gate for integrating the OR-gate output to produce a corresponding D.C. logic level; and
comparator means coupled to the output of said detector means and to a reference voltage for determining whether the D.C. logic level is above or below a predetermined threshold value.

8. The apparatus of claim 1 further comprising:
high impedance means in series with said input terminal for protecting a user from electric shock.

9. Apparatus for tethering personnel to electrical ground and monitoring the integrity of said ground comprising:
a case;
means for strapping said case to a body member such as a wrist;
an input terminal adjacent said case;
means for electrically coupling said input terminal to said body member when said case is strapped to the body member;
circuit means mounted within said case for detecting the presence of an electrical ground at said input terminal; and
means coupled to said circuit means for indicating to a user whether an electrical ground is detected at the input terminal.

10. The apparatus of claim 9 further comprising an electronic watch mounted in said case and having a digital display for displaying the time.

11. The apparatus of claim 10 further comprising:
interface circuitry means coupled between said circuit means and said electronic watch for enabling the watch display to function as the electrical ground indicating means.

12. The apparatus of claim 9 further comprising:
means for indicating to a user whether the coupling means is in proper electrical contact with said body member.

13. The apparatus of claim 12 wherein said contact indicating means comprises:
means for verifying a proper skin conductivity between said coupling means and an additional contact mounted to said case and oriented to contact the body member to which the case is strapped.

14. The apparatus of claim 9 wherein said circuit means comprises:
an oscillator;
means for mixing the output of said oscillator with a signal from said input terminal to provide a composite signal;
an exclusive OR-gate;
means for coupling the composite signal to a first input of said OR-gate;
means for coupling the output of said oscillator to a second input of said OR-gate; and
means for processing the output of said OR-gate to produce an output signal indicative of the phase relationship between said oscillator output and said composite signal;
whereby grounding said input terminal varies the phase relationship between said oscillator output and said composite signal resulting in a change in said output signal.

15. The apparatus of claim 14 further comprising:
means responsive to said output signal for providing a visual indication as to whether said input terminal is grounded.

16. The apparatus of claim 14 further comprising:
means responsive to said output signal for providing an aural indication as to whether said input terminal is grounded.

17. The apparatus of claim 14 further comprising:
delay circuit means coupled between said oscillator output and said exclusive OR-gate for delaying the oscillator output signal by a predetermined time period before it reaches the second input of said OR-gate.

18. The apparatus of claim 14 wherein said processing means comprises:
detector means coupled to the output of said exclusive OR-gate for integrating the OR-gate output to produce a corresponding D.C. logic level; and
comparator means coupled to the output of said detector means and to a reference voltage for determining whether the D.C. logic level is above or below a predetermined threshold value.

19. The apparatus of claim 9 further comprising:
a grounding cable having a main conductor and a conductive shield;
means for coupling the main conductor at a first end of the grounding cable to ground;
means for coupling the main conductor at the other end of the grounding cable to said input terminal; and
means for detecting whether the impedance between said main conductor and shield is proper.

20. The apparatus of claim 19 wherein the main conductor and shield of said grounding cable are connected together at the first end thereof through a resistor of a predetermined value, said resistor forming, in part, the impedance that is detected by said detecting means.

21. The apparatus of claim 19 further comprising:
means coupled to said detecting means for indicating to a user whether a proper impedance has been detected.

22. The apparatus of claim 21 further comprising:
means for indicating to a user whether the means for electrically coupling said input terminal to said body member is in proper electrical contact with said body member.

* * * * *